United States Patent
Tamai et al.

(10) Patent No.: US 6,399,660 B1
(45) Date of Patent: Jun. 4, 2002

(54) AMINOETHYLPHENOXYACETIC ACID DERIVATIVES AND DRUGS FOR PAIN REMISSION AND CALCULI REMOVAL PROMOTION IN URINARY LITHIASIS

(75) Inventors: Tetsuro Tamai; Nobuyuki Tanaka; Hideyuki Muranaka; Harunobu Mukaiyama; Akihito Hirabayashi; Masaaki Sato; Masuo Akahane, all of Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 09/463,432

(22) PCT Filed: May 21, 1999

(86) PCT No.: PCT/JP98/03163

§ 371 (c)(1),
(2), (4) Date: Mar. 31, 2000

(87) PCT Pub. No.: WO99/05090

PCT Pub. Date: Apr. 2, 1999

(30) Foreign Application Priority Data

Jul. 25, 1997 (JP) .............................. 9-233239

(51) Int. Cl.[7] .................. A01N 37/12; A01N 37/44; A61K 31/24; C07C 229/00
(52) U.S. Cl. .................. 514/539; 560/37; 562/442
(58) Field of Search .................. 560/37; 514/539; 562/37, 442

(56) References Cited

U.S. PATENT DOCUMENTS 4,338,333 A * 7/1982 Ainsworth et al. ......... 424/309
5,776,983 A * 7/1998 Washburn et al. .......... 514/605

* cited by examiner

*Primary Examiner*—Gary Geist
*Assistant Examiner*—Zachary C. Tucker
(74) *Attorney, Agent, or Firm*—Sughrue Mion, PLLC

(57) ABSTRACT

Novel aminoethylphenoxyacetic acid derivatives represented by the general formula:

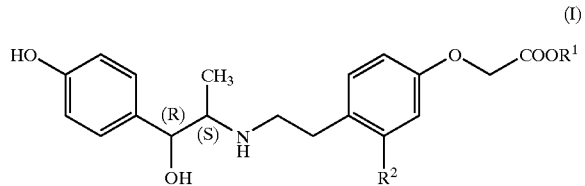

(I)

(wherein $R^1$ represents a hydrogen atom, a lower alkyl group or an aralkyl group; $R^2$ represents a hydrogen atom or a halogen atom; the carbon atom marked with (R) represents a carbon atom in (R) configuration; and the carbon atom marked with (S) represents a carbon atom in (S) configuration) and pharmaceutically acceptable salts thereof, which have stimulating effects on both $\beta_2$- and $\beta_3$-adrenoceptors and are useful as agents for relieving pain and promoting the removal of calculi in urolithiasis.

16 Claims, No Drawings

AMINOETHYLPHENOXYACETIC ACID DERIVATIVES AND DRUGS FOR PAIN REMISSION AND CALCULI REMOVAL PROMOTION IN URINARY LITHIASIS

TECHNICAL FIELD

The present invention relates to aminoethylphenoxyacetic acid derivatives and pharmaceutically acceptable salts thereof which are useful as medicaments.

BACKGROUND ART

Urolithiasis is a disease generating calculi by a series of events such as nucleation of the urinary component, crystallization, aggregation, concretion and enlargement in the lumen of the entire urinary tract from the kidney to the urethra. Urinary flow is often obstructed by calculi, which results in the rise of intra-ureteral pressure, leading to pain. At present, an analgesic and an antispastic are prescribed for the pain. However, the use of the analgesic is only a temporary symptomatic therapy for the pain, and is not expected to treat urolitiasis fundamentally at all. The effectiveness of the antispastic such as an anti-cholinergic is also not satisfactory. Therefore, useful drugs for the causal treatment of urolithiasis, for example, the drugs which relieve pain and promote the removal of calculi by widening the ureter with their strong relaxing effects are desired (The Journal of Urology, Vol.152, pp.1095–1098 (1994)).

It was recently confirmed that both $\beta_2$- and $\beta_3$-adrenoceptors are present in human ureter as $\beta$-adrenoceptor subtypes. It is reported that a drug having stimulating effects on both $\beta_2$- and $\beta_3$-adrenoceptors is extremely useful as an agent for relieving pain and promoting the removal of calculi in urolithiasis because a compound having stimulating effects on both $\beta_2$- and $\beta_3$-adrenoceptors shows potent relaxing effects on ureter (International application publication No. WO97/19700).

DISCLOSURE OF THE INVENTION

The present inventors have studied earnestly to find compounds being useful as agents for relieving pain and promoting the removal of calculi in urolithiasis. As a result, it was found that certain aminoethylphenoxyacetic acid derivatives have potent stimulating effects on both $\beta_2$- and $\beta_3$-adrenoceptors and show excellent ureteral relaxation effects, thereby forming the basis of the present invention.

The present invention relates to aminoethylphenoxyacetic acid derivatives represented by the general formula:

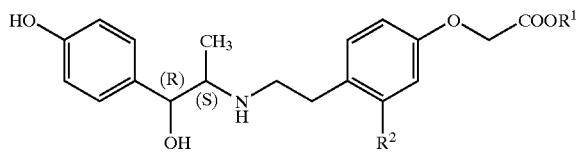

(I)

(wherein $R^1$ represents a hydrogen atom, a lower alkyl group or an aralkyl group; $R^2$ represents a hydrogen atom or a halogen atom; the carbon atom marked with (R) represents a carbon atom in (R) configuration; and the carbon atom marked with (S) represents a carbon atom in (S) configuration) and pharmaceutically acceptable salts thereof.

The present invention relates to pharmaceutical compositions comprising an aminoethylphenoxyacetic acid derivative represented by the above general formula (I) or a pharmaceutically acceptable salt thereof.

The present invention relates to agents for relieving pain and promoting the removal of calculi which comprises as the active ingredient an aminoethylphenoxyacetic acid derivative represented by the above general formula (I) or a pharmaceutically acceptable salt thereof.

The present invention relates to methods for relieving pain and promoting the removal of calculi in urolithiasis which comprises administering a therapeutically effective amount of an aminoethylphenoxyacetic acid derivative represented by the above general formula (I) or a pharmaceutically acceptable salt thereof.

The present invention relates to uses of an aminoethylphenoxyacetic acid derivative represented by the above general formula (I) or a pharmaceutically acceptable salt thereof for the manufacture of a pharmaceutical composition for the treatment of urolithiasis.

The present invention relates to uses of an aminoethylphenoxyacetic acid derivative represented by the above general formula (I) or a pharmaceutically acceptable salt thereof as agents for relieving pain and promoting the removal of calculi in urolithiasis.

The present invention relates to processes for the manufacture of a pharmaceutical composition for the treatment of urolithiasis, characterized in the use, as an essential constituent of said pharmaceutical composition, of an aminoethylphenoxyacetic acid derivative represented by the above general formula (I) or a pharmaceutically acceptable salt thereof.

In the present invention, the term "lower alkyl group" means an alkyl group having from 1 to 6 carbon atoms such as a methyl group, an ethyl group, a propyl group, an isopropyl group, a butyl group, an isobutyl group, a sec-butyl group, a tert-butyl group, a pentyl group and a hexyl group; the term "aralkyl group" means the above lower alkyl group substituted by an aryl group such as a phenyl group and a naphthyl group; and the term "halogen atom" means a fluorine atom, a chlorine atom, a bromine atom and an iodine atom.

The compounds represented by the above general formula (I) of the present invention can be prepared according to the following procedures. For example, the compounds of the present invention can be prepared by subjecting a phenylpropanolamine derivative represented by the formula:

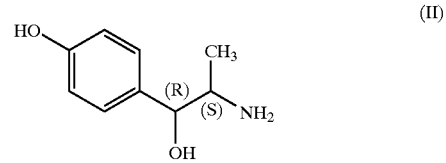

(II)

(wherein the carbon atom marked with (R) and the carbon atom marked with (S) have the same meanings as defined above) to alkylation using an alkylating agent represented by the general formula:

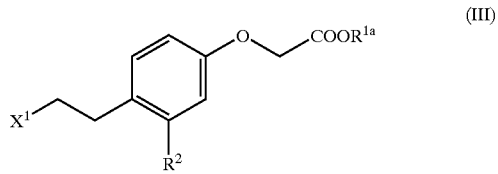

(III)

(wherein $R^{1a}$ represents a lower alkyl group or an aralkyl group; $X^1$ represents a chlorine atom or a bromine atom; and R² has the same meaning as defined above), and hydrolyzing the ester group of the resulting compound in the usual way as occasion demands.

Of the compounds represented by the above general formula (I) of the present invention, compounds represented by the general formula:

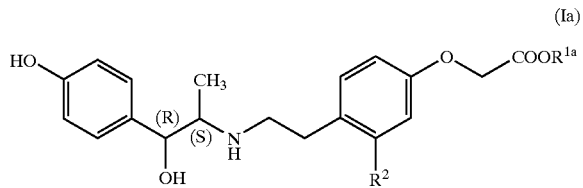

(Ia)

(wherein $R^{1a}$, $R^2$, the carbon atom marked with (R) and the carbon atom marked with (S) have the same meanings as defined above) can be also prepared by esterification of the corresponding aminoethylphenoxyacetic acid derivative (compounds represented by the general formula (Ib) described below).

The phenylpropanolamine derivative represented by the above formula (II) used as a starting material in the above production process can be prepared by optical resolution of a commercially available enantiomeric mixture in the usual way or a method described in a literature (J. Med. Chem., Vol. 20, No. 7, pp. 978–981(1977)).

The alkylating agents represented by the above general formula (III) used as starting materials in the above production process can be prepared by allowing an anisole derivative represented by the general formula:

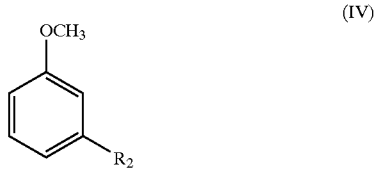

(IV)

(wherein $R^2$ has the same meaning as defined above) to react with a compound represented by the general formula:

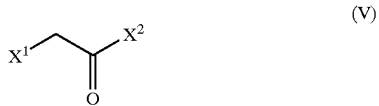

(V)

(wherein $X^2$ represents a chlorine atom or a bromine atom; and $X^1$ has the same meaning as defined above) in the presence of a Lewis acid such as aluminum chloride, removing the methyl group as occasion demands, reducing the carbonyl group using a reducing agent such as triethylsilane to give a phenol derivative represented by the general formula:

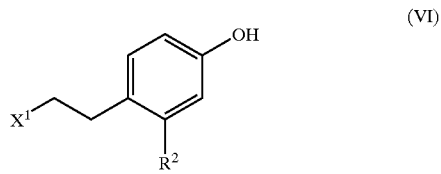

(VI)

(wherein $R^2$ and $X^1$ have the same meanings as defined above), and allowing the resulting compound to react with an alkyl halogenoacetate in the presence of a base such as potassium carbonate.

The aminoethylphenoxyacetic acid derivatives represented by the above general formula (I) of the present invention obtained by the above production processes can be readily isolated and purified by conventional separation means such as fractional recrystallization, purification using column chromatography and solvent extraction.

The aminoethylphenoxyacetic acid derivatives represented by the above general formula (I) of the present invention can be converted into their pharmaceutically acceptable salts in the usual way. Examples of the such salts include acid addition salts formed with mineral acids such as hydrochloric acid, hydrobromic acid, hydroiodic acid, sulfuric acid, nitric acid and phosphoric acid, acid addition salts formed with organic acids such as formic acid, acetic acid, propionic acid, citric acid, tartaric acid, fumalic acid, butyric acid, oxalic acid, succinic acid, malonic acid, maleic acid, lactic acid, malic acid, carbonic acid, glutamic acid, aspartic acid, methanesulfonic acid, benzenesulfonic acid and p-toluenesulfonic acid, inorganic base salts such as a sodium salt, a potassium salt, a calcium salt and an ammonium salt, and salts formed with organic bases such as triethylamine, piperidine, morpholine, pyridine and lysine.

In addition, the compounds represented by the above general formula (I) of the present invention also include their solvates with pharmaceutically acceptable solvents such as water and ethanol.

$\beta_2$-Adrenoceptor stimulating effects of the compounds represented by the above general formula (I) of the present invention can be measured by using pregnant rat uterus. For example, $EC_{50}$ value (the concentration inhibiting 50% of the spontaneous contraction) of 2-[4-[2-[[(1S,2R)-2-hydroxy-2-(4-hydroxyphenyl)-1-methylethyl]amino]ethyl] phenoxy]-acetic acid was $3.1 \times 10^{-8}$M.

$\beta_3$-Adrenoceptor stimulating effects of the compounds represented by the above general formula (I) of the present invention can be measured by using ferret ureter. For example, $EC_{50}$ value (the concentration inhibiting 50% of the spontaneous contraction) of 2-[4-[2-[[(1S,2R)-2-hydroxy-2-(4-hydroxyphenyl)-1-methylethyl]amino]ethyl] phenoxy]-acetic acid was $1.4 \times 10^{-8}$M.

Thus, the compounds represented by the above general formula (I) of the present invention have potent stimulating effects on both $\beta_2$- and $\beta_3$-adrenoceptors and are useful as agents for relieving pain and promoting the removal of calculi such as spontaneous passage of calculi and the removal of the calculi after extracorporeal shock wave lithotripsy in urolithiasis.

In the present invention, compounds with less $\beta_1$-adrenoceptor stimulating effects in comparison with the above $\beta_2$- and $\beta_3$-adrenoceptor stimulating effects are preferable so as to reduce burdens on the heart and not to induce side effects such as tachycardia. Some compounds of the present invention are $\beta_2$- and $\beta_3$-adrenoceptor stimulants with less $\beta_1$-adrenoceptor stimulating effects. As examples of such compounds, compounds represented by the general formula:

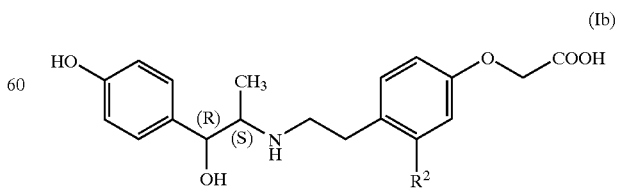

(Ib)

(wherein $R^2$, the carbon atom marked with (R) and the carbon atom marked with (S) have the same meanings as defined above) and pharmaceutical acceptable salts thereof can be illustrated.

As more preferable compounds in the present invention, 2-[4-[2-[[(1S,2R)-2-hydroxy-2-(4-hydroxyphenyl)-1-methylethyl]amino]-ethyl]phenoxy]acetic acid, 2-[3-fluoro-4-[2-[[(1S,2R)-2-hydroxy-2-(4-hydroxyphenyl)-1-methylethyl]amino]ethyl]phenoxy]acetic acid and pharmaceutically acceptable salts thereof can be illustrated.

For example, in the experiment for measuring $\beta_1$-adrenoceptor stimulating effects using rat atrium, 2-[4-[2-[[(1S,2R)-2-hydroxy-2-(4-hydroxyphenyl)-1-methylethyl]amino]ethyl]phenoxy]acetic acid showed $EC_{A20}$ value (the concentration to increase the heart rate by 20 beats per minute) at a concentration of $1.3 \times 10^{-6}$ M.

Furthermore, the compounds represented by the above general formula (I) of the present invention are highly safe. For example, in acute toxicity test using rats, any dead rats were not observed by a single administration of 1,000 mg/kg of 2-[4-[2-[[(1S,2R)-2-hydroxy-2-(4-hydroxyphenyl)-1-methylethyl]amino]ethyl]phenoxy]acetic acid.

In consequence, the compounds represented by the above general formula (I) of the present invention and pharmaceutically acceptable salts thereof have potent and extremely useful stimulating effects on both $\beta_2$- and $\beta_3$-adrenoceptors.

When the aminoethylphenoxyacetic acid derivatives represented by the above general formula (I) of the present invention and pharmaceutically acceptable salts thereof are employed in the practical treatment, they are administered orally or parenterally in the form of appropriate pharmaceutical compositions such as tablets, powders, fine granules, granules, capsules, injections and the like. These pharmaceutical compositions can be formulated in accordance with conventional methods using conventional pharmaceutical carriers, excipients and other additives.

The dosage is appropriately decided depending on the sex, age, body weight, degree of symptoms and the like of each patient to be treated, which is approximately within the range of from 1 to 1,000 mg per day per adult human in the case of oral administration and approximately within the range of from 0.01 to 100 mg per day per adult human in the case of parenteral administration, and the daily dose can be divided into one to several doses per day.

BEST MODE FOR CARRYING OUT THE INVENTION

The present invention is further illustrated in more detail by way of the following Reference Examples, Examples and Test Examples. The present invention is not limited thereto.

Reference Example 1

2'-Fluoro-4'-hydroxyphenacyl bromide

To a stirred suspension of aluminum chloride (17.5 g) in 1,2-dichloroethane (146 ml) was added bromoacetyl bromide (3.8 ml) under ice-cooling. After the mixture was stirred for 30 minutes, 3-fluoro-anisole (5.0 ml) was added to the reaction mixture and the resulting mixture was stirred for 12 hours at room temperature. The reaction mixture was poured into ice-water and extracted with dichloromethane. The extract was washed with water and dried over anhydrous magnesium sulfate. After solvent was removed in vacuo, purification of the residue by medium pressure liquid column chromatography on silica gel (eluent: hexane/ethyl acetate=4/1) gave 2'-fluoro-4'-hydroxyphenacyl bromide (518 mg).

$^1$H-NMR (CDCl$_3$) δppm: 4.78 (2H, s), 5.74 (1H, br s), 6.63 (1H, dd, J=12.5, 2.4 Hz), 6.73 (1H, dd, J=8.7, 2.4 Hz), 7.92 (1H, t, J=8.7 Hz)

Reference Example 2

2'-Chloro-4'-hydroxyphenacyl bromide

2'-Chloro-4'-methoxyphenacyl bromide was prepared using 3-chloroanisole according to a similar manner to that described in Reference Example 1.

$^1$H-NMR (CDCl$_3$) δppm: 3.86 (3H, s), 4.54 (2H, s), 6.88 (1H, dd, J=8.7, 2.5 Hz), 6.96 (1H, d, J=2.5 Hz), 7.69 (1H, d, J=8.7 Hz)

2'-Chloro-4'-methoxyphenacyl bromide (451 mg) was dissolved in 1,2-dichloroethane (8.6 ml). Aluminium chrolide (690 mg) was added to the solution at room temperature with stirring, and the mixture was stirred for 3 hours at 60° C. The reaction mixture was poured into ice-water and extracted with ethyl acetate. The extract was washed with brine and dried over anhydrous magnesium sulfate. After the solvent was removed in vacuo, purification of the residue by medium pressure liquid column chromatography on silica gel (eluent: hexane/ethyl acetate=3/1) gave 2'-chloro-4'-hydroxyphenacyl bromide (295 mg).

$^1$H-NMR (CDCl$_3$) δppm: 4.54 (2H, s), 5.77 (1H, s), 6.82 (1H, dd, J=8.6, 2.4 Hz), 6.94 (1H, d, J=2.4 Hz), 7.65 (1H, d, J=8.6 Hz)

Reference Example 3

4-(2-Bromoethyl)-3-chlorophenol

To a stirred solution of 2'-chloro-4'-hydroxyphenacyl bromide (291 mg) in dichloromethane (6.0 ml) were added trifluoroacetic acid (900 μl) and triethylsilane (610 μl) at room temperature, and the mixture was heated under reflux for 3 hours. A saturated aqueous sodium bicarbonate solution was added to the reaction mixture and the resulting mixture was extracted with ethyl acetate. The extract was washed with water and dried over anhydrous magnesium sulfate. After the solvent was removed in vacuo, purification of the residue by medium pressure liquid column chromatography on silica gel (eluent: hexane/ethyl acetate=5/1) gave 4-(2-bromoethyl)-3-chlorophenol (183 mg).

$^1$H-NMR (CDCl$_3$) δppm: 3.21 (2H, t, J=7.5 Hz), 3.55 (2H, t, J=7.5 Hz), 5.01 (1H, s), 6.70 (1H, dd, J=8.3, 2.6 Hz), 6.88 (1H, d, J=2.6 Hz), 7.12 (1H, d, J=8.3 Hz)

Reference Example 4

4-(2-Bromoethyl)-3-fluorophenol 4-(2-Bromoethyl)-3-fluorophenol was prepared using 2'-fluoro-4'-hydroxyphenacyl bromide according to a similar manner to that described in Reference Example 3.

$^1$H-NMR (CDCl$_3$) δppm: 3.12 (2H, t, J=7.5 Hz), 3.53 (2H, t, J=7.5 Hz), 6.50–6.60 (2H, m), 7.00–7.10 (1H, m)

Reference Example 5

Ethyl 2-[4-(2-bromoethyl)-3-chlorophenoxy]acetate

To a stirred solution of 4-(2-bromoethyl)-3-chlorophenol (158 mg) in acetone (7 ml) were added potassium carbonate (139 mg) and ethyl bromoacetate (89 μl) at room temperature. After the mixture was stirred for 20 hours at room temperature, the insoluble material was filtered off and the filtrate was concentrated in vacuo. Purification of the residue by medium pressure liquid column chromatography on silica gel (eluent: hexane/ethyl acetate 7/1) gave ethyl 2-[4-(2-bromoethyl)-3-chlorophenoxy]acetate (193 mg).

$^1$H-NMR (CDCl$_3$) δppm: 1.30 (3H, t, J=7.1 Hz), 3.22 (2H, t, J=7.5 Hz), 3.55 (2H, t, J=7.5 Hz), 4.28 (2H, q, J=7.1

Hz), 4.59 (2H, s), 6.78 (1H, dd, J=8.5, 2.7 Hz), 6.94 (1H, d, J=2.7 Hz), 7.17 (1H, d, J=8.5 Hz)

Reference Example 6

The following compounds were prepared using the corresponding bromoacetic acid derivative and phenol derivative according to a similar manner to that described in Reference Example 5.

Ethyl 2-[4-(2-bromoethyl)phenoxy]acetate $^1$H-NMR (CDCl$_3$) δppm: 1.30 (3H, t, J=7.1 Hz), 3.10 (2H, t, J=7.6 Hz), 3.53 (2H, t, J=7.6 Hz), 4.27 (2H, q, J=7.1 Hz), 4.61 (2H, s), 6.86 (2H, d, J=8.5 Hz), 7.13 (2H, d, J=8.5 Hz)

Ethyl 2-[4-(2-bromoethyl)-3-fluorophenoxy]acetate $^1$H-NMR (CDCl$_3$) δppm: 1.30 (3H, t, J=7.1 Hz), 3.13 (2H, t, J=7.5 Hz), 3.53 (2H, t, J=7.5 Hz), 4.28 (2H, q, J=7.1 Hz), 4.59 (2H, s), 6.60–6.70 (2H, m), 7.12 (1H, t, J=8.6 Hz)

Benzyl 2-[4-(2-bromoethyl)-3-fluorophenoxy]acetate $^1$H-NMR (CDCl$_3$) δppm: 3.13 (2H, t, J=7.5 Hz), 3.53 (2H, t, J=7.5 Hz), 4.64 (2H, s), 5.24 (2H, s), 6.55–6.70 (2H, m), 7.11 (1H, t, J=8.7 Hz)

Example 1

Ethyl 2-[3-chloro-4-[2-[[(1S,2R)-2-hydroxy-2-(4-hydroxyphenyl)-1-methylethyl]amino]ethyl] phenoxy]acetate (Compound 1)

A solution of (1R,2S)-2-amino-1-(4-hydroxyphenyl) propan-1-ol (97 mg), ethyl 2-[4-(2-bromoethyl)-3-chlorophenoxy]acetate (187 mg) and N,N-diisopropylethylamine (203 μl) in N,N-dimethylformamide (3 ml) was stirred for 10 hours at 60° C. After cooling, water was added to the reaction mixture and the resulting mixture was extracted with ethyl acetate. The extract was washed with water and dried over anhydrous magnesium sulfate. After the solvent was removed in vacuo, purification of the residue by medium pressure liquid column chromatography on aminopropyl silica gel (eluent: ethyl acetate/ethanol=30/1) gave ethyl 2-[3-chloro-4-[2-[[(1S,2R)-2-hydroxy-2-(4-hydroxyphenyl)-1-methyl-ethyl]amino]ethyl]phenoxy] acetate (75 mg).

$^1$H-NMR (CDCl$_3$) δppm: 0.93 (3H, d, J=6.4 Hz), 1.33 (3H, t, J=7.1 Hz), 2.75–3.05 (5H, m), 4.31 (2H, q, J=7.1 Hz), 4.53 (1H, d, J=5.2 Hz), 4.60 (2H, s), 6.65–6.80 (3H, m), 6.88 (1H, d, J=2.7 Hz), 7.03 (1H, d, J=8.5 Hz), 7.10 (2H, d, J=8.2 Hz)

Example 2

The following compounds were prepared using the corresponding phenoxyacetate derivative according to a similar manner to that described in Example 1.

Ethyl 2-[4-[2-[[(1S,2R)-2-hydroxy-2-(4-hydroxyphenyl)-1-methyl-ethyl]amino]ethyl] phenoxy]acetate (Compound 2)

$^1$H-NMR (CDCl$_3$) δppm: 0.97 (3H, d, J=6.4 Hz), 1.33 (3H, t, J=7.1 Hz), 2.60–2.80 (4H, m), 2.90–3.05 (1H, m), 4.31 (2H, q, J=7.1 Hz), 4.47 (1H, d, J=5.6 Hz), 4.62 (2H, s), 6.69 (2H, d, J=8.6 Hz), 6.76 (2H, d, J=8.6 Hz), 7.01 (2H, d, J=8.6 Hz), 7.05 (2H, d, J=8.6 Hz)

Ethyl 2-[3-fluoro-4-[2-[[(1S,2R)-2-hydroxy-2-(4-hydroxyphenyl)-1-methylethyl]amino]ethyl] phenoxy]acetate (Compound 3)

$^1$H-NMR (DMSO-d$_6$) δppm: 0.81 (3H, d, J=6.3 Hz), 1.22 (3H, t, J=7.1 Hz), 2.55–2.80 (5H, m), 4.18 (2H, q, J=7.1 Hz), 4.35–4.45 (1H, m), 4.78 (2H, s), 4.80–4.90 (1H, m), 6.65–6.80 (4H, m), 7.05–7.20 (3H, m), 9.18 (1H, br)

Benzyl 2-[3-fluoro-4-[2-[[(1S,2R)-2-hydroxy-2-(4-hydroxyphenyl)-1-methylethyl]amino]ethyl] phenoxy]acetate (Compound 4)

$^1$H-NMR (DMSO-d$_6$) δppm: 0.80 (3H, d, J=6.4 Hz), 1.30 (1H, br), 2.55–2.80 (5H, m), 4.41 (1H, br s), 4.80–4.95 (3H, m), 5.20 (2H, s), 6.60–6.80 (4H, m), 7.00–7.20 (3H, m), 7.25–7.45 (5H, m), 9.20 (1H, br)

Example 3

Ethyl 2-[3-chloro-4-[2-[[(1S,2R)-2-hydroxy-2-(4-hydroxyphenyl)-1-methylethyl]amino]ethyl] phenoxy]acetate hydrochloride (Compound 5)

To a stirred solution of ethyl 2-[3-chloro-4-[2-[[(1S,2R)-2-hydroxy-2-(4-hydroxyphenyl)-1-methylethyl]amino] ethyl]phenoxy]-acetate (120 mg) in ethyl acetate (2.0 ml) was added 4N hydrogen chloride ethyl acetate solution (220 μl) under ice-cooling, and the mixture was vigorously stirred for an hour at room temperature. Collection of the resulting precipitates by filtration gave ethyl 2-[3-chloro-4-[2-[[(1S,2R)-2-hydroxy-2-(4-hydroxyphenyl)-1-methylethyl]amino] ethyl]-phenoxy]acetate hydrochloride (110 mg).

$^1$H-NMR (DMSO-d$_6$) δppm: 0.96 (3H, d, J=6.9 Hz), 1.22 (3H, t, J=7.2 Hz), 3.05–3.20 (4H, m), 3.25–3.40 (1H, m), 4.17 (2H, q, J=7.2 Hz), 4.82 (2H, s), 5.06 (1H, br), 5.97 (1H, d, J=3.8 Hz), 6.76 (2H, d, J=8.2 Hz), 6.95 (1H, dd, J=8.8, 2.7 Hz), 7.08 (1H, d, J=2.7 Hz), 7.17 (2H, d, J=8.2 Hz), 7.33 (1H, d, J=8.8 Hz), 8.89 (2H, br), 9.42 (1H, s)

Specific rotation: $[\alpha]_D^{25}$=−9.20° (c=0.50, Methanol)

Example 4

The following compounds were prepared according to a similar manner to that described in Example 3 using the corresponding phenoxyacetic acid derivatives.

Ethyl 2-[3-fluoro-4-[2-[[(1S,2R)-2-hydroxy-2-(4-hydroxyphenyl)-1-methylethyl]amino]ethyl] phenoxy]acetate hydrochloride (Compound 6)

$^1$H-NMR (DMSO-d$_6$) δppm: 0.95 (3H, d, J=6.6 Hz), 1.22 (3H, t, J=7.1 Hz), 2.90–3.05 (2H, m), 3.10–3.40 (3H, m), 4.17 (2H, q, J=7.1 Hz), 4.81 (2H, s), 5.03 (1H, br s), 5.97 (1H, d, J=3.8 Hz), 6.70–6.85 (3H, m), 6.87 (1H, dd, J=12.0, 2.3 Hz), 7.17 (2H, d, J=8.4 Hz), 7.27 (1H, t, J=8.7 Hz), 8.75 (2H, br), 9.41 (1H, s)

Specific rotation: $[\alpha]_D^{32}$=−10.0° (c=0.74, Methanol)

Benzyl 2-[3-fluoro-4-[2-[[(1S,2R)-2-hydroxy-2-(4-hydroxyphenyl)-1-methylethyl]amino]ethyl] phenoxy]acetate hydrochloride (Compound 7)

$^1$H-NMR (DMSO-d$_6$) δppm: 0.95 (3H, d, J=6.6 Hz), 2.95–3.45 (5H, m), 4.90 (2H, s), 5.03 (1H, br s), 5.20 (2H, s), 5.98 (1H, br s), 6.70–6.85 (3H, m), 6.88 (1H, dd, J=12.0, 2.2 Hz), 7.17 (2H, d, J=8.4 Hz), 7.26 (1H, t, J=8.8 Hz), 7.30–7.45 (5H, m), 8.80 (2H, br), 9.41 (1H, s)

Specific rotation: $[\alpha]_D^{32}$=−8.70° (c=1.20, Methanol)

Example 5

2-[3-Chloro-4-[2-[[(1S,2R)-2-hydroxy-2-(4-hydroxyphenyl)-1-methyl-ethyl]amino]ethyl] phenoxy]acetic acid (Compound 8)

To a stirred solution of ethyl 2-[3-chloro-4-[2-[[(1S,2R)-2-hydroxy-2-(4-hydroxyphenyl)-1-methylethyl]amino]

ethyl]phenoxy]-acetate (63 mg) in ethanol (775 µl) was added 1N aqueous sodium hydroxide solution (465 µl) at room temperature. After the mixture was stirred for 20 hours, 1N hydrochloric acid (465 µl) was added to the reaction mixture under ice-cooling with stirring. Collection of the resulting precipitates by filtration gave 2-[3-chloro-4-[2-[[(1S,2R)-2-hydroxy-2-(4-hydroxyphenyl)-1-methylethyl]amino]ethyl]phenoxy]-acetic acid (44 mg).

$^1$H-NMR (DMSO-$d_6$+$D_2O$) δppm: 0.90 (3H, d, J=6.6 Hz), 2.30–2.80 (2H, m), 2.90–3.05 (2H, m), 3.20–3.35 (1H, m), 4.30–4.45 (2H, m), 5.05–5.15 (1H, m), 6.70–6.80 (3H, m), 6.86 (1H, d, J=2.5 Hz), 6.94 (1H, d, J=8.6 Hz), 7.16 (2H, d, J=8.5 Hz)

Specific rotation: $[\alpha]_D^{25}$=−5.7° (c=0.56, 1N hydrochloric acid)

Example 6

The following compounds were prepared using the corresponding phenoxyacetic acid derivative according to a similar manner to that described in Example 5.

2-[4-[2-[[(1S,2R)-2-Hydroxy-2-(4-hydroxyphenyl)-1-methylethyl]-amino]ethyl]phenoxy]acetic acid (Compound 9)

$^1$H-NMR (DMSO-$d_6$) δppm: 0.91 (3H, d, J=6.6 Hz), 2.55–2.75 (2H, m), 2.90–3.05 (2H, m), 3.15–3.25 (1H, m), 4.34 (2H, s), 5.00–5.10 (1H, m), 6.65–6.80 (4H, m), 6.91 (2H, d, J=8.6 Hz), 7.13 (2H, d, J=8.6 Hz), 9.40 (1H, br)

Specific rotation: $[\alpha]_D^{25}$=−10.00° (c=1.06, 1N hydrochloric acid)

2-[3-Fluoro-4-[2-[[(1S,2R)-2-hydroxy-2-(4-hydroxyphenyl)-1-methyl-ethyl]amino]ethyl]phenoxy]acetic acid (Compound 10)

$^1$H-NMR (DMSO-$d_6$) δppm: 0.87 (3H, d, J=6.6 Hz), 2.30–2.70 (2H, m), 2.85–3.00 (2H, m), 3.15–3.30 (1H, m), 4.30–4.50 (2H, m), 5.00–5.15 (1H, m), 6.55–6.70 (2H, m), 6.71 (2H, d, J=8.6 Hz), 6.88 (1H, t, J=8.8 Hz), 7.13 (2H, d, J=8.6 Hz), 9.40 (2H, br)

Specific rotation: $[\alpha]_D^{25}$=−6.60° (c=1.19, Acetic acid)

Example 7

Benzyl 2-[3-chloro-4-[2-[[(1S,2R)-2-hydroxy-2-(4-hydroxyphenyl)-1-methylethyl]amino]ethyl]phenoxy]acetate hydrochloride (Compound 11)

A solution of 2-[3-chloro-4-[2-[[(1S,2R)-2-hydroxy-2-(4-hydroxyphenyl)-1-methylethyl]amino]ethyl]phenoxy]acetic acid (200 mg) and methanesulfonic acid (38 µl) in benzyl alcohol (1.0 ml) was stirred for 2 days at room temperature. Purification of the reaction mixture by medium pressure liquid column chromatography on aminopropyl silica gel (eluent: ethyl acetate/ethanol=20/1) gave benzyl 2-[3-chloro-4-[2-[[(1S,2R)-2-hydroxy-2-(4-hydroxyphenyl)-1-methylethyl]amino]ethyl]-phenoxy]acetate (136 mg).

$^1$H-NMR (CDCl$_3$) δppm: 0.95 (3H, d, J=6.3 Hz), 2.75–3.05 (5H, m), 4.54 (1H, d, J=5.0 Hz), 4.63 (2H, s), 5.25 (2H, s), 6.65–6.75 (3H, m), 6.86 (1H, d, J=2.5 Hz), 7.00 (1H, d, J=8.5 Hz), 7.08 (2H, d, J=8.5 Hz), 7.30–7.45 (5H, m)

To a stirred solution of benzyl 2-[3-chloro-4-[2-[[(1S,2R)-2-hydroxy-2-(4-hydroxyphenyl)-1-methylethyl]amino]ethyl]phenoxy]-acetate (136 mg) in ethyl acetate (2.0 ml) was added 4N hydrogen chloride ethyl acetate solution (161 µl) under ice-cooling, and the mixture was vigorously stirred for an hour at room temperature. Collection of the resulting precipitates by filtration gave benzyl 2-[3-chloro-4-[2-[[(1S,2R)-2-hydroxy-2-(4-hydroxyphenyl)-1-methylethyl]amino]ethyl]-phenoxy]acetate hydrochloride (137 mg).

$^1$H-NMR (DMSO-$d_6$) δppm: 0.96 (3H, d, J=6.9 Hz), 3.00–3.20 (4H, m), 3.30–3.45 (1H, m), 4.92 (2H, s), 5.03 (1H, br), 5.20 (2H, s), 5.97 (1H, br s), 6.76 (2H, d, J=8.8 Hz), 6.96 (1H, dd, J=8.2, 2.7 Hz), 7.09 (1H, d, J=2.7 Hz), 7.18 (2H, d, J=8.8 Hz), 7.30–7.45 (6H, m), 8.75 (2H, br), 9.38 (1H, s)

Specific rotation: $[\alpha]_D^{25}$=−6.40° (c=0.53, Methanol)

Example 8

The following compounds were prepared using 2-[4-[2-[[(1S,2R)-2-hydroxy-2-(4-hydroxyphenyl)-1-methylethyl]amino]ethyl]phenoxy]-acetic acid according to a similar manner to that described in Example 7.

Benzyl 2-[4-[2-[[(1S,2R)-2-hydroxy-2-(4-hydroxyphenyl)-1-methyl-ethyl]amino]ethyl]phenoxy]acetate (Compound 12)

$^1$H-NMR (CDCl$_3$) δppm: 0.93 (3H, d, J=6.5 Hz), 2.65–2.85 (4H, m), 2.90–3.05 (1H, m), 4.49 (1H, d, J=5.2 Hz), 4.66 (2H, s), 5.27 (2H, s), 6.70 (2H, d, J=8.6 Hz), 6.76 (2H, d, J=8.6 Hz), 7.01 (2H, d, J=8.6 Hz), 7.06 (2H, d, J=8.6 Hz), 7.30–7.40 (5H, m)

Benzyl 2-[4-[2-[[(1S,2R)-2-hydroxy-2-(4-hydroxyphenyl)-1-methyl-ethyl]amino]ethyl]phenoxy]acetate hydrochloride (Compound 13)

$^1$H-NMR (DMSO-$d_6$) δppm: 0.95 (3H, d, J=6.7 Hz), 2.90–3.00 (2H, m), 3.10–3.40 (3H, m), 4.85 (2H, s), 5.03 (1H, br s), 5.19 (2H, s), 5.97 (1H, d, J=4.0 Hz), 6.76 (2H, d, J=8.5 Hz), 6.91 (2H, d, J=8.7 Hz), 7.16 (2H, d, J=8.5 Hz), 7.19 (2H, d, J=8.7 Hz), 7.30–7.45 (5H, m), 8.70 (2H, br), 9.41 (1H, s)

Specific rotation: $[\alpha]_D^{25}$=−8.30° (c=0.51, Methanol)

Test Example 1

$\beta_2$-Adrenoceptor Stimulating Effects

Uteri of pregnant SD rats (pregnancy day 21) were isolated and longitudinal smooth muscle strips of approximately 15 mm in length and approximately 5 mm in width free from the basal plate were prepared. The experiment was conducted according to the Magnus method. The preparations with a tension of 1 g were exposed to Locke-Ringer solution maintained at 37° C. and gassed with a mixture of 95% oxygen and 5% carbon dioxide. Spontaneous contractions of myometrium were isometrically measured with a force-displacement transducer and recorded by a rectigraph. The drug was cumulatively added to the Magnus bath every 5 minutes. The drug efficacy was evaluated as the concentration of the drug required to produce 50% of the inhibition of uterine contractions (i.e., $EC_{50}$ value) by comparing the sum of uterine contractions during 5 minutes after the addition of the drug with the sum of uterine contractions during 5 minutes before the addition of the drug (100%). The result was shown in the following Table.

Test Example 2

$\beta_3$-Adrenoceptor Stimulating Effects

Ureters of male ferrets (1100 to 1400 g in body weght) were isolated. After removal of connective tissue, longitudinal smooth muscle strips of approximately 20 mm in length were prepared. The experiment was conducted according to the Magnus method. The preparations with a tension of 0.5 g were exposed to Krebs-Henseleit solution maintained at 37° C. and gassed with a mixture of 95% oxygen and 5% carbon dioxide. Spontaneous contractions of ureters were isometrically measured with a force-displacement transducer and recorded by a rectigraph. The drug was cumulatively added to the Magnus bath every 3 minutes. The drug efficacy was evaluated as the concentration of the drug required to produce 50% of the inhibition of ureter contractions (i.e., $EC_{50}$ value) by comparing the sum of ureter contractions during 3 minutes after the addition of the drug with the sum of ureter contractions during 3 minute before addition of the drug (100%). The result was shown in the following Table.

Test Example 3

$\beta_1$-Adrenoceptor-stimulating Effects

Atria of male SD rats (350 to 400 g in body weight) were isolated and the experiment was conducted according to the Magnus methods. The preparations with a tension of 1 g were exposed to Krebs-Henseleit solution maintained at 37° C. and gassed with a mixture of 95% oxygen and 5% carbon dioxide. The cardiac contractility was isometrically measured with a force-displacement transducer and recorded by a rectigraph. The drug efficacy was evaluated as the molar concentration required to produce 20 beats/minute increment of the heart rate (i.e., $EC_{A20}$ value). The result was shown in the following Table.

| Compound No. | Test Example 1 (M) | Test Example 2 (M) | Test Example 3 (M) |
| --- | --- | --- | --- |
| 7 | $3.3 \times 10^{-9}$ | $3.5 \times 10^{-8}$ | $3.0 \times 10^{-7}$ |
| 8 | $1.3 \times 10^{-8}$ | $4.1 \times 10^{-9}$ | $1.1 \times 10^{-7}$ |
| 9 | $3.1 \times 10^{-8}$ | $1.4 \times 10^{-8}$ | $1.3 \times 10^{-6}$ |
| 10 | $3.9 \times 10^{-8}$ | $6.8 \times 10^{-9}$ | $1.0 \times 10^{-6}$ |

Test Example 4

Acute Toxicity Test

To male ICR rats of 4 weeks age was administered 1,000 mg/kg of 2-[4-[2-[[(1S,2R)-2-hydroxy-2-(4-hydroxyphenyl)-1-methylethyl]-amino]ethyl]phenoxy] acetic acid intravenously by a single administration. Any dead rats were not observed during 24 hours after the administration with the time course.

INDUSTRIAL APPLICABILITY

The aminoethylphenoxyacetic acid derivatives and pharmaceutically acceptable salts thereof represented by the above general formula (I) of the present invention have stimulating effects on both $\beta_2$- and $\beta_3$-adrenpceptors and show potent ureteral relaxtion effects. Therefore, the compounds of the present invention are extremely useful compounds as medicaments such as agents for relieving pain and promoting the removal of calculi in urolithiasis.

What is claimed is:

1. An aminoethylphenoxyacetic acid derivative represented by the general formula:

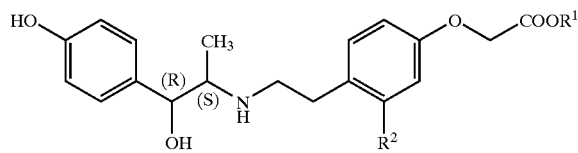

(wherein $R^1$ represents a hydrogen atom, a lower alkyl group or an aralkyl group; $R^2$ represents a hydrogen atom or a halogen atom; the carbon atom marked with (R) represents a carbon atom in (R) configuration; and the carbon atom marked with (S) represents a carbon atom in (S) configuration) or a pharmaceutically acceptable salt thereof.

2. An aminoethylphenoxyacetic acid derivative as claimed in claim 1, represented by the general formula:

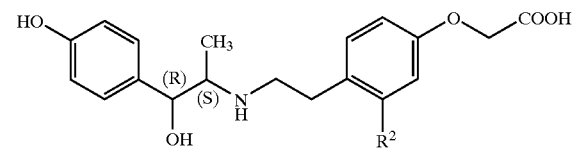

(wherein $R^2$ represents a hydrogen atom or a halogen atom; the carbon atom marked with (R) represents a carbon atom in (R) configuration; and the carbon atom marked with (S) represents a carbon atom in (S) configuration) or a pharmaceutically acceptable salt thereof.

3. 2-[4-[2-[[(1S,2R)-2-Hydroxy-2-(4-hydroxyphenyl)-1-methyl-ethyl]amino]ethyl]phenoxy]acetic acid as claimed in claim 2 or a pharmaceutically acceptable salt thereof.

4. 2-[3-Fluoro-4-[2-[[(1S,2R)-2-hydroxy-2-(4-hydroxyphenyl)-1-methylethyl]amino]ethyl]phenoxy]acetic acid as claimed in claim 2 or a pharmaceutically acceptable salt thereof.

5. A pharmaceutical composition comprising an aminoethylphenoxyacetic acid derivative as claimed in claim 1 or a pharmaceutically acceptable salt thereof.

6. An agent for relieving pain and promoting the removal of calculi in urolithiasis which comprises as the active ingredient an amino-ethylphenoxyacetic acid derivative as claimed in claim 1 or a pharmaceutically acceptable salt thereof.

7. A method for relieving pain and promoting the removal of calculi in urolithiasis which comprises administering a therapeutically effective amount of an aminoethylphenoxyacetic acid derivative as claimed in claim 1 or a pharmaceutically acceptable salt thereof.

8. A pharmaceutical composition comprising an aminoethylphenoxyacetic acid derivative as claimed in claim 2 or a pharmaceutically acceptable salt thereof.

9. A pharmaceutical composition comprising an aminoethylphenoxyacetic acid derivative as claimed in claim 3 or a pharmaceutically acceptable salt thereof.

10. A pharmaceutical composition comprising an aminoethylphenoxyacetic acid derivative as claimed in claim 4 or a pharmaceutically acceptable salt thereof.

11. An agent for relieving pain and promoting the removal of calculi in urolithiasis which comprises as the active ingredient an aminoethylphenoxyacetic acid derivative as claimed in claim 2 or a pharmaceutically acceptable salt thereof.

12. An agent for relieving pain and promoting the removal of calculi in urolithiasis which comprises as the active ingredient an aminoethylphenoxyacetic acid derivative as claimed in claim 3 or a pharmaceutically acceptable salt thereof.

13. An agent for relieving pain and promoting the removal of calculi in urolithiasis which comprises as the active ingredient an aminoethylphenoxyacetic acid derivative as claimed in claim 4 or a pharmaceutically acceptable salt thereof.

14. A method for relieving pain and promoting the removal of calculi in urolithiasis which comprises administering a therapeutically effective amount of an aminoethylphenoxyacetic acid derivative as claimed in claim 2 or a pharmaceutically acceptable salt thereof.

15. A method for relieving pain and promoting the removal of calculi in urolithiasis which comprises administering a therapeutically effective amount of an aminoethylphenoxyacetic acid derivative as claimed in claim 3 or a pharmaceutically acceptable salt thereof.

16. A method for relieving pain and promoting the removal of calculi in urolithiasis which comprises administering a therapeutically effective amount of an aminoethylphenoxyacetic acid derivative as claimed in claim 4 or a pharmaceutically acceptable salt thereof.

* * * * *

UNITED STATES PATENT AND TRADEMARK OFFICE
CERTIFICATE OF CORRECTION

PATENT NO. : 6,399,660 B1
DATED : June 4, 2002
INVENTOR(S) : Tetsuro Tamai et al.

It is certified that error appears in the above-identified patent and that said Letters Patent is hereby corrected as shown below:

<u>Title page,</u>
Item [22], PCT Filed, please delete "May 21, 1999" and insert therefor -- July 15, 1998 --

Signed and Sealed this

Eleventh Day of February, 2003

JAMES E. ROGAN
*Director of the United States Patent and Trademark Office*